United States Patent [19]

Hsieh et al.

[11] Patent Number: 5,628,739
[45] Date of Patent: May 13, 1997

[54] PREBENT ANATOMICALLY SHAPED SELF-ALIGNING SANITARY NAPKIN

[75] Inventors: Tong-Ho J. Hsieh, East Brunswick; John T. Ulman, Woodbridge, both of N.J.

[73] Assignee: McNeil-PPC, Inc., Skillman, N.J.

[21] Appl. No.: 410,550

[22] Filed: Mar. 24, 1995

Related U.S. Application Data

[63] Continuation of Ser. No. 8,016, Jan. 22, 1993, abandoned.
[51] Int. Cl.⁶ .............................. A61F 13/15; A61F 13/20
[52] U.S. Cl. .................... 604/385.1; 604/372; 604/387
[58] Field of Search ..................................... 604/358, 372, 604/373, 378, 385.1, 385.2, 387, 389

[56] References Cited

U.S. PATENT DOCUMENTS

| 2,331,355 | 10/1943 | Strongson | 128/290 |
|---|---|---|---|
| 2,747,575 | 5/1956 | Mercer | 604/385.1 |
| 3,575,174 | 4/1971 | Mogor | 604/385.1 |
| 3,736,931 | 6/1973 | Glassman | 604/385.1 |
| 4,340,058 | 7/1982 | Pierce et al. | 604/385.1 |
| 4,490,147 | 12/1984 | Pierce et al. | 604/385.1 X |
| 4,540,414 | 9/1985 | Wishman | 604/378 |
| 4,573,990 | 3/1986 | Ohsaki | 604/385 |
| 4,595,392 | 6/1986 | Johnson et al. | 604/385 |
| 4,631,062 | 12/1986 | Lassen et al. | 604/385.1 |
| 4,655,759 | 4/1987 | Romans-Hess et al. | 604/385 |
| 4,673,403 | 6/1987 | Lassen et al. | 604/385.1 |
| 4,701,177 | 10/1987 | Ellis et al. | 604/385 |
| 4,790,838 | 12/1988 | Pigneul et al. | 604/385.1 X |
| 4,804,380 | 2/1989 | Lassen et al. | 604/385.1 |
| 4,897,084 | 1/1990 | Ternstrom et al. | 604/385.2 |
| 4,935,021 | 6/1990 | Huffman et al. | 604/385.1 |
| 5,004,465 | 4/1991 | Terström et al. | 604/378 |
| 5,057,096 | 10/1991 | Faglione | 604/385.1 |
| 5,098,422 | 3/1992 | Davis et al. | 604/385.1 |
| 5,127,911 | 7/1992 | Baharav | 604/385.1 |
| 5,171,302 | 12/1992 | Buell | 604/385.1 |

FOREIGN PATENT DOCUMENTS

| 0335252A2 | 10/1989 | European Pat. Off. |
| 0335253A1 | 10/1989 | European Pat. Off. |
| 0405403A2 | 1/1991 | European Pat. Off. |

Primary Examiner—John G. Weiss
Assistant Examiner—P. Zuttarelli
Attorney, Agent, or Firm—James P. Barr

[57] ABSTRACT

Prebent, anatomically shaped, self-aligning absorbent products comprising a fluid permeable body facing cover, an absorbent element, a central, partially longitudinally disposed core, and a flexible, moisture barrier having partially longitudinally disposed permanent creases proximate to the longitudinal edges of the moisture barrier, are provided. Such products generally have a convex shape in the approximate center portion of the body facing surface which shape allows the product to conform to the body and more closely approximate the source of fluid discharge thereby reducing unwanted movement or misalignment which may result in leakage. Such products further generally have an hourglass shape which complements the general contour of the inside surfaces of the thighs.

17 Claims, 2 Drawing Sheets

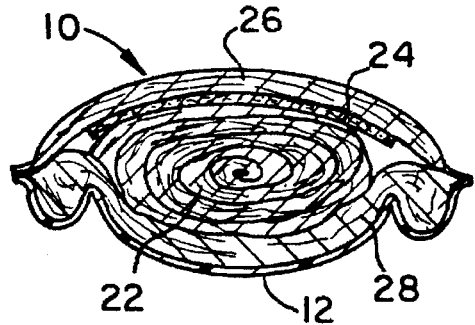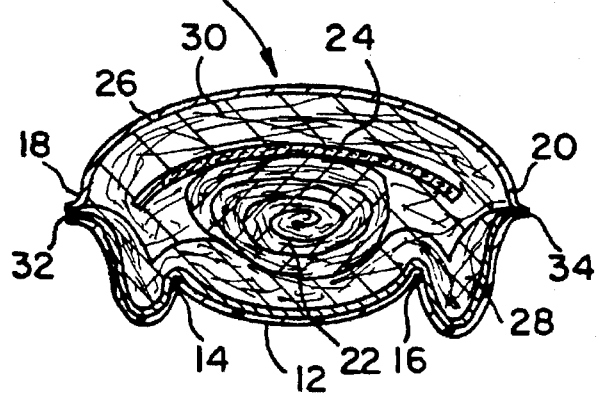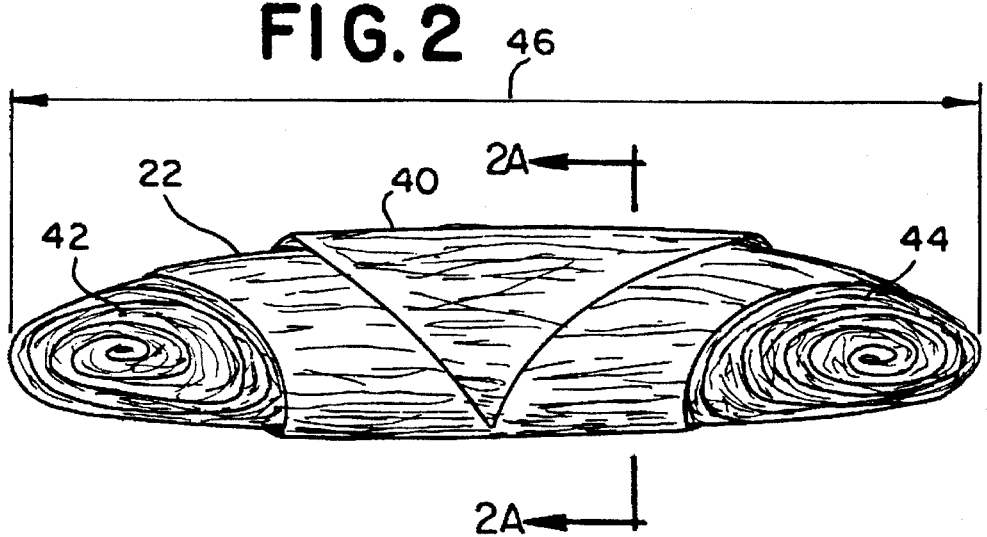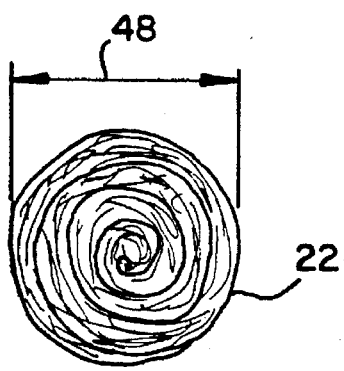

PREBENT ANATOMICALLY SHAPED SELF-ALIGNING SANITARY NAPKIN

This is a continuation of application Ser. No. 08/008,016, filed Jan. 22, 1993 now abandoned.

FIELD OF THE INVENTION

The present invention relates to absorbent products, especially anatomically shaped absorbent products.

BACKGROUND OF THE INVENTION

There is a continuing effort to improve absorbent products, such as diapers, sanitary napkins, wound dressings, bandages, incontinent pads and the like, that absorb body fluids and contain them well without leakage. Generally, it is preferred that such absorbent products be soft and readily conform to body contours.

A persistent problem with traditional absorbent products, especially feminine napkins, is that they are molded to the anatomy by pressure of the body and pressure from the panty. When the wearer pulls up her undergarment with the pad attached, pressure is put onto the pad when it comes in contact with the body. When the wearer sits down, her body weight forces the product to conform to her body shape. The absorbent filler, which is normally ground wood pulp, is forced to shift because of its loose structure of short fibers. When the pad is compressed to the shape by the body, the pulp yields and distorts in many directions. Such distorting can cause the pad to move off center or to either side thereby compromising its function as a fluid absorbent. The distorting, shifting pad is poorly fitting and incorrectly placed. The misplacement of the pad results in misalignment with the source of the fluid discharge and causes early product failure.

The recognition that the function of absorbent products is compromised by unwanted movement of the pad prompted the development of form-fitting absorbent products. For example, U.S. Pat. No. 4,804,380, issued Feb. 14, 1989, in the name of Lassen, et al., discloses a catamenial device having a length greater than about seven inches and having a fold at its longitudinal center of the back one-half to two-thirds of the device. The peak like shape of the back portion is said to mold to the perineum and the buttocks.

European Patent Application Publication No. 0 405 403 A2, discloses a panty-liner having at least one longitudinal fold which allows an adaptation of the width of the liner. The design allows adjustment of the width of the liner to conform to the width of the crotch of the panty.

U.S. Pat. No. 2,331,355, issued Oct. 12, 1943, in the name of Herman Strongson, discloses a catamenial pad having extra thickness at the central longitudinal portion. The central portion of the pad is gathered upwardly, and held in position by horizontal stitching through the base.

U.S. Pat. No. 2,747,575, issued May 29, 1956, in the name of Berton Mercer, discloses a catamenial pad having a longitudinal medial portion bulged to form a hump.

U.S. Pat. No. 4,573,990, issued Mar. 4, 1986, in the name of Hiroaki Ohsaki, discloses a disposable diaper being folded along its longitudinal center line into a generally inverted Ω-shaped vertical cross sectional configuration.

U.S. Pat. No. 4,595,392, issued Jun. 17, 1986, in the names of Johnson and Lassen, discloses an interlabial pad having a cylindrodially-shaped central portion. The pad is formed by folding a pad blank along the central longitudinal axis and gathering and attaching the blank below the fold line to form a cylindrodially shaped center with radial flaps.

U.S. Pat. No. 4,655,759, issued Apr. 7, 1987, in the name of Romans-Hess, et al., discloses a catamenial pad with embossed channels adjacent to the longitudinal edges of the napkin to reduce side leakage.

U.S. Pat. No. 4,701,177, issued Oct. 20, 1987, in the name of Ellis, et al., discloses an absorbent pad shaped generally in an hourglass configuration with a middle portion somewhat thicker than the absorbent portions at the ends of the pad. The pad is provided with upstanding side portions in the middle of each long edge where the absorbent is narrower.

U.S. Pat. No. 4,790,838, issued Dec. 13, 1988, in the names of Pigneul and Ruppel, discloses a device for forming a sanitary pad having a central biconcave area of reduced width.

U.S. Pat. No. 4,897,084, issued Jan. 30, 1990, in the names of Ternstrom and Lundahl, discloses an absorbent article having elastic threads arranged in a V-shaped pattern, wherein the V-shaped patterns diverge from the center of one end of the article to the corners of the article at its opposite end, thereby forming a basin or pocket which extends along the whole length of the article.

U.S. Pat. No. 4,935,021, issued Jun. 19, 1990, in the names of Huffman and Pieniak, discloses a disposable diaper having a center gathering means for providing a longitudinal gathering force.

U.S. Pat. No. 5,057,096, issued Oct. 15, 1991, in the name of Frances Faglione, discloses a genital vulva pad/sanitary napkin wherein the vulva pad member is dimensioned and configured to fit inside a woman's vulva and releasably secured to the sanitary napkin by flexible tangs.

U.S. Pat. No. 5,127,911, issued Jul. 7, 1992, in the name of Eva Baharav, discloses a sanitary napkin having a mechanism comprising a string means which allows a user the option of forming a contoured projection in the napkin by drawing together part of the longitudinal edges of the napkin so as to form a labial feminine pad to be interposed within the labia majora of the user of the pad.

European Patent Application Publication Nos. 0 335 253 A1 and 0 335 252 A2, are directed to disposable absorbent articles having a flexure-resistant deformation. The sanitary napkins have a convex upward configuration, which configuration relies on the lateral compressive forces of the wearer's thighs to form or maintain the configuration.

It has also been suggested that the problems of unwanted movement, roping, and twisting may be overcome by fixing the pad to the undergarment more securely. U.S. Pat. No. 5,098,422, issued Mar. 24, 1992, in the name of Davis, et al., discloses an absorbent product having a semi-rigid clip means for retaining the absorbent product with respect to an undergarment.

Despite advances in absorbent products, currently available products continue to exhibit problems such as leakage attributed to unwanted movement or distortion of the pad. Accordingly, there is a need for absorbent structures designed to improve the fit of the absorbent product to the body, thereby reducing unwanted movement or misalignment which may result in leakage.

It is an object of this invention to provide prebent, anatomically shaped absorbent products that are self-aligning to maintain correct placement of the pad on the body. Such products generally have a convex shape in the approximate center portion of the body facing surface which shape allows the product to conform to the body.

SUMMARY OF THE INVENTION

The present invention provides prebent, anatomically shaped, self-aligning absorbent products. Such absorbent products generally comprise a fluid permeable body facing cover, an absorbent element, a central, partially longitudinally disposed core, and a flexible, moisture barrier having partially longitudinally disposed permanent creases proximate to the longitudinal edges of the moisture barrier. Such products generally have a convex shape in the approximate center portion of the body facing surface which shape allows the product to conform to the body and more closely approximate the source of fluid discharge thereby reducing unwanted movement or misalignment which may result in leakage. Such products further generally have an hourglass shape which complements the general contour of the inside surfaces of the thighs.

BRIEF DESCRIPTION OF THE DRAWINGS

FIGS. 1 and 1A are cross-sectional views of absorbent pads of this invention.

FIG. 2 is an illustration of the central, partially longitudinally disposed core of an absorbent pad of this invention.

FIG. 2A is a cross-sectional view of the central, partially longitudinally disposed core of an absorbent pad of this invention.

DETAILED DESCRIPTION OF THE INVENTION

Figure 3:
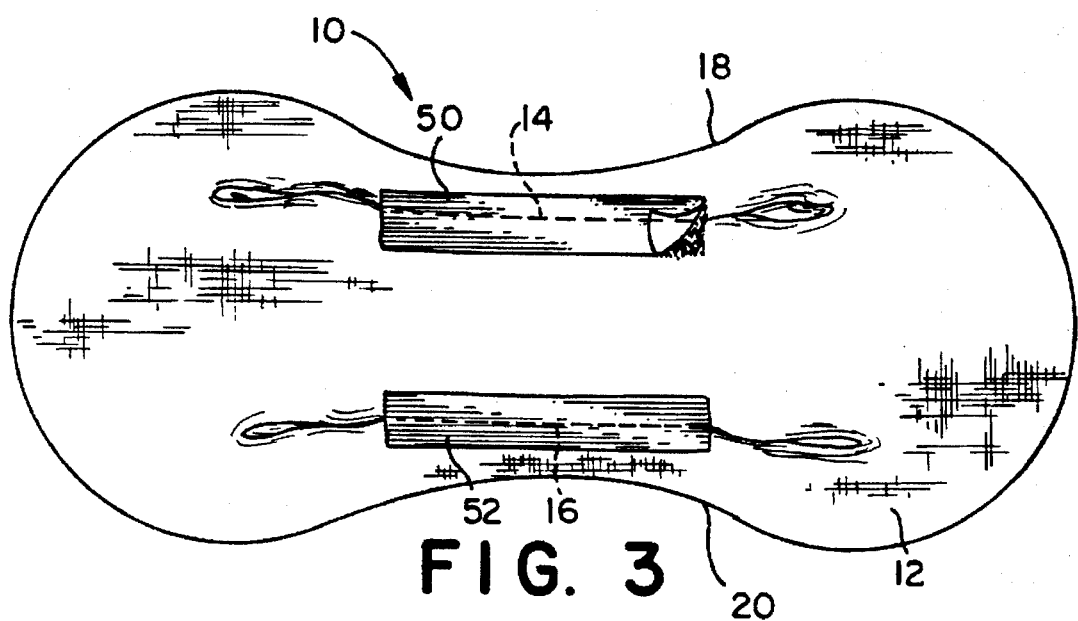
FIG. 3 is an illustration of the garment facing side of the moisture barrier of an absorbent pad of this invention.

Generally, the absorbent pads provided by the present invention comprise a fluid permeable body facing cover, an absorbent element, a central, partially longitudinally disposed core, and a flexible, moisture barrier having partially longitudinally disposed permanent creases proximate to the longitudinal edges of the garment facing side of the moisture barrier. The key features of these absorbent products include the central, partially longitudinally disposed core, and the partially longitudinally disposed permanent creases proximate to the longitudinal edges of the garment facing side of the moisture barrier. These elements provide the absorbent products with a convex shape in the approximate center portion of the body facing surface which shape allows the product to conform to the body and more closely approximate the source of fluid discharge.

In this invention, the central, partially longitudinally disposed core may comprise a roll or cable of resilient material. The roll or cable is thickest in its middle portion and has tapered ends. The roll or cable does not extend for the entire length of the pad, but rather is partially longitudinally disposed in the approximate center of the pad. This reduces the thickness of the pad at either end of the pad thereby allowing the product to cup the labia and fold into the buttock.

The partially longitudinally disposed permanent creases also do not extend for the length of the pad, but rather are partially longitudinally disposed on either side of the approximate center of the pad. The creases generally decrease the width of the middle portion of each of the longitudinal edges of the pad thereby causing the pad to assume a contoured or hourglass shape.

The central, partially longitudinally disposed core and partially longitudinally disposed creases cause the product to have a convex shape from both a cross-sectional view and a longitudinally-sectional view. This shape allows the pad to closely approximate the source of fluid discharge thereby reducing unwanted movement or misalignment which may result in leakage.

Referring now to the embodiments illustrated in the drawings, FIGS. 1 and 1A, are cross-sectional views of an absorbent pad 10 having a flexible moisture barrier 12 which is provided with partially longitudinally disposed permanent creases 14 and 16 proximate to the longitudinal edges 18 and 20 of the garment facing side of the pad 10. The pad 10 has a central, partially longitudinally disposed core 22 comprising a roll or cable of resilient material extending partially longitudinally in the approximate center of the pad 10. The pad has an absorbent element 24 and a fluid permeable body facing cover 26.

In a preferred embodiment, the pad 10 is further provided with a layer of resilient material 28 secured to the body facing side of the moisture barrier 12 and stretching across the width of the absorbent pad 10. This layer of resilient material 28 helps define creases 14 and 16. This layer of resilient material 28 may be secured to the moisture barrier 12 by methods known to those in the art. Such methods may include securing the resilient layer 28 to the moisture barrier 12 with glue. The pad 10 may also, optionally, be provided with a moisture permeable coverstock 30 on the body facing side of the body facing cover 26.

Illustrated in FIG. 2, is the central, partially longitudinally disposed core 22 comprising a resilient material which material may be rolled such that the approximate center portion 40 of the core 22, the thickest portion of the core occurring at about the center of the length 46 of the core 22, is thicker than ends 42 and 44 of the core 22. A core 22 of this shape may be formed by rolling a square of resilient material from corner to corner. A core of this shape may also be formed by extruding a cable of resilient material using methods known to those in the art.

Figure 2B:
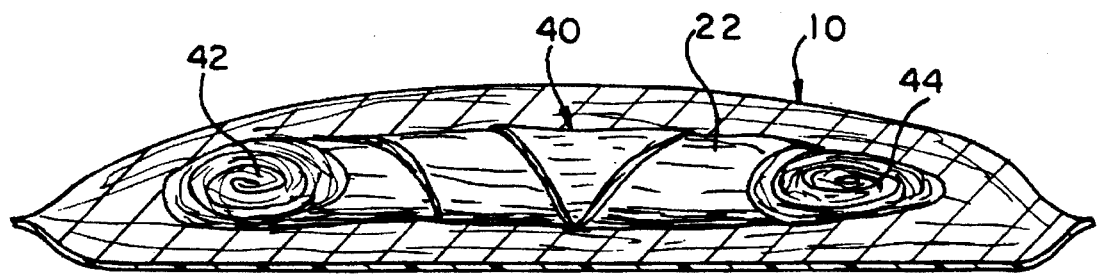
FIG. 2B is a longitudinal-sectional view of an absorbent pad of this invention.

The core 22 does not extend for the entire length of the pad 10, but rather is partially longitudinally disposed in the approximate center of the pad. FIG. 2B is a longitudinal-sectional view of the pad 10 which shows that because the approximate center 40 of the core 22 is thicker than the ends 42 and 44, and the core 22 does not extend for the entire length of the pad 10, the pad 10 assumes a longitudinally convex shape. This shape allows the product to cup the labia and fold into the buttock.

In preferred embodiments, the approximate center 40 of the core 22 has a diameter 48 of between about ½ inch and 1½ inches, and the core 22 has a length 46 of between about 3 inches and 4½ inches. In one embodiment, the approximate center 40 of the core 22 has a diameter 48, as illustrated in FIG. 2A, of about ¾ inches and the core 22 has a length 46 of about 4 inches.

FIG. 3 is an illustration of the garment facing side of the moisture barrier 12 which shows permanent creases 14 and 16 partially longitudinally disposed on the garment facing side of the moisture barrier 12. Such creases may be formed, for example, by adhesive or heat stitching. The adhesive may be a hot melt adhesive, either pressure sensitive or not.

In one embodiment, the garment facing side of the moisture barrier 12 is provided with two strips of adhesive which strips are each from about 1 inch to 1¾ inches in length and have a distance of between about 1½ inches and 1¾ inches between them, which distance is measured from the approximate center of one adhesive strip to the approximate center of the other adhesive strip. Using methods known to those skilled in the art, a folding tool may be utilized to put pressure on the moisture barrier 12 to form the partially longitudinally disposed creases 14 and 16. Utilizing a folding tool, the moisture barrier 12 is pushed in from the sides at the flange seal areas 32 and 34 thereby forcing the moisture barrier 12 into an inverted "V" shaped crease with the adhesive strips being incorporated in the creases 14 and 16. This decreases the width of the middle portion of each of the longitudinal edges 18 and 20 of the pad thereby causing the pad to assume a contoured or hourglass shape which shape is complementary to the shape of the medial aspects of the thighs. This shape allows the pad to self-align and makes it easier to keep the pad centered.

In a preferred embodiment, the adhesive strips are each about 1 inch in length and have a distance of about 1.6 inches between them, which distance is measured from the approximate center of one adhesive strip to the approximate center of the other adhesive strip. However, different shaped adhesive patterns may be used and the spacing between the adhesive strips varied with the shape of the pad.

On the underside of the moisture barrier 12, on the side of the pad facing the wearer's undergarment, there may be placed adhesive attachment means 50 and 52 for temporarily, but securely, adhering the pad to the crotch portion of that garment. The attachment means may comprise adhesive lines covered with release strips which, when peeled from the adhesive strips, leave the adhesive tacky. Alternately, the attachment means may comprise pressure-sensitive adhesive tape, said tape having a first face permanently adhered to the shell and an opposite second face adapted to be temporarily attached to the nether garment.

Turning now to a more detailed description of the components of the pads of this invention, the body facing cover 26 of the pad generally comprises a film or fabric having a high degree of moisture permeability. Films made from hydrophobic bicomponent fibers, for example, polyester/polyester and polyester/polyethylene, are especially suitable. A typical hydrophobic bicomponent fiber has a polyester core and a polyethylene sheath. Preferably, the fabric used for the body facing cover is a lightweight fabric in the range of 0.3 to 5.0 oz. per square yard and with a density less than 0.2 gms/cc. The most suitable fabrics have unusually high elongation, loft, softness and drape characteristics. Films which are perforated or noncontinuous are also satisfactory. Though the cover is moisture permeable, it is preferably of the type which after permeation of the moisture, prevents strike-back of the body fluid when the absorbent structure is approaching saturation. The body facing cover is readily sealable to the outer rim of the moisture barrier, for example, by a heat seal or printed adhesive. The body facing cover may have different characteristics such as an embossed texture.

The absorbent element 24 may comprise any absorbent capable of absorbing human exudate. For example, the absorbent element may comprise a sheet of tenderized peat moss made by methods well known in the art. Generally, the raw peat moss material utilized is peat moss of the sphagnum variety and is preferably capable of absorbing at least about 15 times, preferably about 20 times, its weight in water. The peat moss is generally screened and then separated into a usable fraction and peat fines. The screened peat moss may be combined with other absorbent materials, preferably fibrous and cellulosic in nature. These art-recognized materials may include Kraft, wood pulp and mechanical wood pulp. This material is generally a chemically treated, long fibered pulp such as sulfite and sulfate wood pulps. A suitable mixture of ingredients for the absorbent elements of the invention may comprise from about 5 to about 20 percent by weight of Kraft wood pulp, with the remainder being essentially peat moss. Generally, the absorbent element is about ⅛ to ¼ inch thick. It is understood that those familiar with the art may find a wide range of peat moss compositions as well as other absorbent materials for use with the products of this invention. Examples include but are not limited to blends of wood pulp fiber and superabsorbent materials, and laminates of wet-laid or air-laid pulp fabrics and superabsorbent.

The core 22 and layer of material 28 independently comprise a resilient material, for example, a polyester fiber such as Kem-Wove, manufactured by Kem-Wove, Inc. For the purposes of this invention, it is preferred that the material employed has good wet stability. Other materials, non-wovens, bicomponent fibers, and the like, may be employed by the present invention, provided that such materials are able to maintain the convex shape of the product during use. It has been found that when a square of material, such as Kenwove, having a base weight of about 1½ oz. per square yard, is air bonded and rolled from corner to corner as described herein, it has the strength to maintain the convex shape of the pad during use.

The moisture barrier 12 may be any flexible, liquid permeable material. Especially suitable are liquid-impermeable polyolefin films, e.g., polyethylene or polyethylene terephthalate.

On the underside of the barrier there may be placed adhesive attachment means for temporarily, but securely, adhering the shell to the crotch portion of the wearer's nether garment. The attachment means may comprise adhesive lines covered with release strips which, when peeled from the adhesive strips, leave the adhesive tacky. Alternately, the attachment means may comprise pressure-sensitive adhesive tape, said tape having a first face permanently adhered to the shell and an opposite second face adapted to be temporarily attached to the nether garment.

In a preferred embodiment of the invention, a fibrous layer 30 is interposed between absorbent element 24 and moisture-permeable cover 26. This fibrous layer preferably comprises heat-fusible hydrophobic fibers or a blend of heat-fusible hydrophobic fibers and hydrophilic fibers. Examples of hydrophobic fibers include polyester/polyester, polyester/polyethylene and polyethylene/polyester bicomponent fibers. Examples of hydrophilic fiber include rayon, cotton and wood pulp fibers. The ratio of hydrophobic to hydrophilic fiber can vary, but, in the preferred embodiment, a greater amount of hydrophobic than hydrophilic fiber is utilized. Fibrous layer 30, containing heat-fusible fibers, may be stabilized by exposure to heat. It is also preferred to fuse cover 26 to the fibrous layer, and this can be accomplished by utilizing a cover material made from a fusible fiber, such as a polyethylene/polyester bicomponent fabric. A particular example is a fabric called "Enka", available from Johnson & Johnson Worldwide Absorbent Products Company. Cover material 26 is placed over fibrous layer 30, and the combination is exposed to heat. This fuses the fibers in both fibrous layer 30 and cover material 26, stabilizing fibrous layer 30 and fusing cover 26 to said fibrous layer.

The combination of cover material 26 and fibrous layer 30 may be thermoformed create a desired topography, for example, a pattern of longitudinal channels to wick discharged fluid longitudinally and prevent lateral wicking. For example, cover material 26 may be placed on a screen with the desired cover topography, and the fibers of which layer 30 is comprised are placed on top of cover material 26. A vacuum is applied to pull the materials into the shape of the screen, and the material is then heated to fuse the hydrophobic fibers. See the disclosure in U.S. Pat. No. 5,540,872 issued Jul. 30, 1996, the disclosure of which is herein incorporated by reference.

From the foregoing, it will be observed that numerous variations and modifications may be effected without departing from the true spirit and scope of the novel concept of this invention.

We claim:

1. An absorbent pad comprising longitudinal and transverse edges, a center portion located between and approximately equidistant from each longitudinal edge and between and approximately equidistant from each transverse edge, a fluid permeable body facing cover having a body facing side and a garment facing side, an absorbent element, a central, partially longitudinally disposed core, and a flexible, moisture barrier having a garment facing side and a body facing side and having partially longitudinally disposed permanent creases proximate to the longitudinal edges of the garment facing side of said moisture barrier, wherein said absorbent pad has a convex shape in the center portion of the body facing cover.

2. The absorbent pad of claim 1 wherein said central, partially longitudinally disposed core comprises a resilient material which material is rolled such that the center portion of said core is thicker than the transverse edges of said core.

3. The absorbent pad of claim 2 wherein said center portion of said core has a diameter of between about ½ inch and 1½ inches, and said core has a length of between about 3 inches and 4½ inches.

4. The absorbent pad of claim 3 wherein said center portion of said core has a diameter of about ¾ inches and said core has a length of about 4 inches.

5. The absorbent pad of claim 1 wherein said central, partially longitudinally disposed core comprises a cable of resilient material which cable is thickest in the center portion and has tapered ends.

6. The absorbent pad of claim 5 wherein the center portion of said cable has a diameter of between about ½ inch and 1½ inches and said cable has a length of between about 3 inches and 4½ inches.

7. The absorbent pad of claim 6 wherein said center portion of said cable has a diameter of about ¾ inches and said cable has a length of about 4 inches.

8. The absorbent pad of claim 1 wherein each of said partially longitudinally disposed permanent creases is formed with adhesive.

9. The absorbent pad of claim 8 wherein said adhesive is a hot melt adhesive.

10. The absorbent pad of claim 8 wherein said adhesive is provided to the garment facing side of said moisture barrier in two strips which strips are each from about 1 inch to 1¾ inches in length and have a distance of between about 1½ inches and 1¾ inches between them, said distance being measured from the approximate center of one adhesive strip to the center of the other adhesive strip.

11. The absorbent pad of claim 10 wherein said adhesive strips are each about 1 inch in length and have a distance of about 1.6 inches between them, said distance being measured from the approximate center of one adhesive strip to the approximate center of the other adhesive strip.

12. The absorbent pad of claim 1 wherein each of said partially longitudinally disposed permanent creases is formed by heat stitching.

13. The absorbent pad of claim 1 further comprising a layer of resilient material secured to the body facing side of said moisture barrier and stretching across the width of said absorbent pad.

14. The absorbent pad of claim 13 wherein said resilient material is secured to said body facing side of said moisture barrier with glue.

15. The absorbent pad of claim 1 further comprising a moisture permeable coverstock on the body facing side of said body facing cover.

16. The absorbent pad of claim 1 wherein the garment facing side of said moisture barrier is provided with adhesive which may be used to secure said absorbent pad to an undergarment.

17. The absorbent pad of claim 1 further comprising a layer of resilient material secured to the body facing side of said moisture barrier and stretching transversely across said pad and a moisture permeable coverstock on the body facing side of said body facing cover.

* * * * *